United States Patent [19]

Doub et al.

[11] 3,948,903
[45] Apr. 6, 1976

[54] SUBSTITUTED N-(1,2-DIHYDRO-2-OXONICOTINYL)-CEPHALEXINS AND -CEPHALOGLYCINS

[75] Inventors: Leonard Doub; James S. Kaltenbronn, both of Ann Arbor, Mich.

[73] Assignee: Parke, Davis & Company, Detroit, Mich.

[22] Filed: Nov. 11, 1974

[21] Appl. No.: 522,569

Related U.S. Application Data

[63] Continuation-in-part of Ser. No. 315,632, Dec. 15, 1972, Pat. No. 3,873,523.

[52] U.S. Cl. 260/243 C; 260/295.5 R; 260/295.5 T; 424/246
[51] Int. Cl.² .................................. C07D 501/34
[58] Field of Search ......................... 260/243 C

[56] References Cited
UNITED STATES PATENTS

| | | | |
|---|---|---|---|
| 3,308,120 | 3/1967 | Takano et al. | 260/243 C |
| 3,360,515 | 12/1967 | Takano et al. | 260/243 C |
| 3,433,784 | 3/1969 | Long et al. | 260/239.1 |

*Primary Examiner*—Alton D. Rollins
*Assistant Examiner*—Diana G. Rivers

[57] ABSTRACT

Novel organic amide compounds which are substituted N-(1,2-dihydro-2-oxonicotinyl)-ampicillins, -cephalexins and -cephaloglycins having broad spectrum antibacterial utility are provided by (a) reacting the free amino acid ampicillin, cephalexin or cephaloglycin or the acid salt or silylated derivative thereof with a reactive derivative of the corresponding 1,2-dihydro-2-oxonicotinic acid or (b) reacting the free amino acid 6-aminopenicillanic acid, 7-aminocephalosporanic acid or 7-amino-3-methylceph-3-em-4-carboxylic acid or the acid salt or silylated derivative thereof with a reactive derivative of the corresponding N-(1,2-dihydro-2-oxonicotinyl)-2-phenylglycine.

9 Claims, No Drawings

SUBSTITUTED N-(1,2-DIHYDRO-2-OXONICOTINYL)-CEPHALEXINS AND -CEPHALOGLYCINS

CROSS REFERENCE TO RELATED APPLICATIONS

This application is a Continuation-in-Part of copending application Ser. No. 315,632 filed Dec. 15, 1972, and issued as Pat. No. 3,873,523 dated Mar. 25, 1975.

SUMMARY AND DETAILED DESCRIPTION

The present invention relates to novel chemical compounds that are useful as pharmacological agents and to methods for their production. More particularly, the invention relates to novel organic amide compounds having the formula

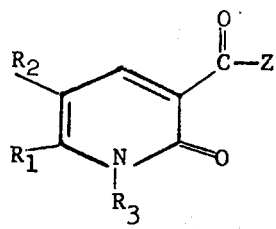

and pharmaceutically-acceptable salts thereof; where $R_1$ is cyclopentylmethyl, cyclopentenylmethyl, cyclohexyl, cyclohexylmethyl, benzyl, phenethyl, adamantyl, methoxybenzyl, hydroxybenzyl, chlorobenzyl, furfuryl, thenyl, pyridyl, furyl or thienyl; $R_2$ is hydrogen or together with $R_1$ represents the group

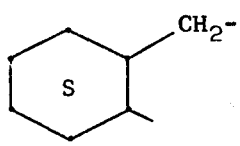

or the group

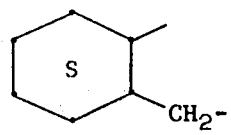

$R_3$ is hydrogen or methyl; and Z is one of three groups having the respective formulas

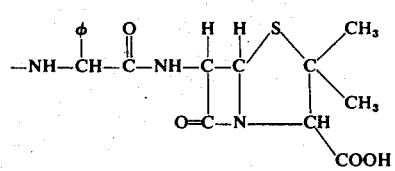

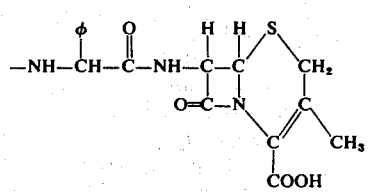

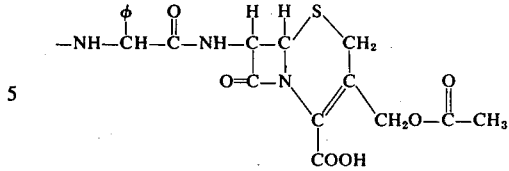

In accordance with the invention the foregoing amide compounds having the formula

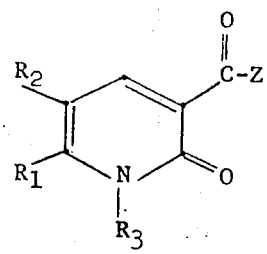

are produced by reacting the free amino acid ampicillin, cephalexin or cephaloglycin or the acid salt or silylated derivative thereof, with a 1,2-dihydro-2-oxonicotinic acid compound having the formula

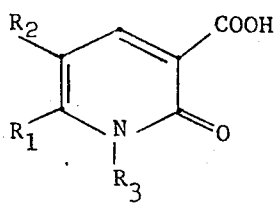

or a reactive derivative thereof; where $R_1$, $R_2$, $R_3$ and Z all have the aforementioned significance. For the reaction the 1,2-dihydro-2-oxonicotinic acid can be employed in activated form by use in known manner of carbodiimide such as N,N'-dicyclohexylcarbodiimide. Some examples of reactive derivatives of the 1,2-dihydro-2-oxonicotinic acid compound suitable for the reaction are the acid halides, the imidazolide, mixed anhydrides (especially those formed from an alkyl chloroformate such as ethyl chloroformate and isobutyl chloroformate), and activated esters such as the pentachlorophenyl ester. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent must be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, using ampicillin, cephalexin and cephaloglycin for the reaction in the free acid or salt form, aqueous solutions may be used for acylation with an acid halide or mixed anhydride under normal Schotten-Baumann conditions. The duration and temperature of the reaction are not critical. Temperatures in the range from −10° to 25° C. are commonly used for reaction times ranging from a few hours up to a day or more. The product may be isolated in any suitable way as the free acid or as a salt by appropriate adjustment of the pH. A preferred procedure is to extract the product in aqueous solution at a pH in the range from 2 to 2.5 with a suitable water-immiscible solvent such as ethyl acetate. In the case where the substituent $R_1$ is pyridyl the extraction is best accomplished in the range from 2.7 to 3.5. As another example of the isolation of the product, the reaction mixture can be evaporated to dryness and the residue treated with acetone to separate and remove any insoluble material. The acetone solution containing the product is then evaporated to give a second residue, which is dissolved in water and the aqueous solution is acidified to a pH in the range from about 2 to 2.5. This acidic solution is extracted with ethyl acetate and the ethyl acetate solution may be evaporated to give the product in the form of the free acid. Alternatively, the ethyl acetate solution may be treated with potassium or sodium 2-ethylhexanoate and the product usually precipitates; if not, the solution then can be concentrated to small volume and treated with ether to precipitate a carboxylate salt.

The 1,2-dihydro-2-oxonicotinic acid compounds and their reactive derivatives which are required as starting materials in the foregoing process can be prepared according to any of a variety of methods as illustrated in greater detail hereinafter. The silylated amino acid starting materials can be prepared by reacting the amino acid (ampicillin, cephalexin or cephaloglycin, or a salt thereof) in anhydrous form with either one or two equivalents of a tri(lower alkyl) silyl chloride in the presence of triethylamine. The preferred silylating agent is trimethylsilyl chloride. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the amide compounds having the formula

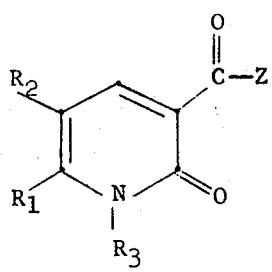

are produced by reacting the free amino acid 6-aminopenicillanic acid, 7-aminocephalosporanic acid or 7-amino-3-methylceph-3-em-4-carboxylic acid or the corresponding acid salt or silylated derivative thereof with a N-(1,2-dihydro-2-oxonicotinyl)-2-phenylglycine having the formula

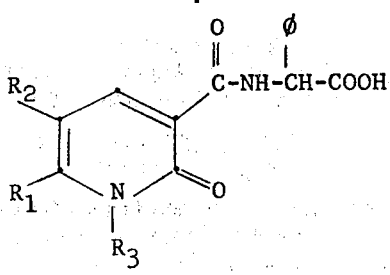

or a reactive derivative thereof, where $R_1$, $R_2$, $R_3$ and Z have the aforementioned significance.

Some examples of reactive derivatives of the N-(1,2-dihydro-2-oxonicotinyl)-2-phenylglycine compounds suitable for the reaction are the acid halides, the imidazolide, mixed anhydrides (especially those formed from an alkyl chloroformate such as ethyl chloroformate and isobutyl chloroformate), and activated esters such as the pentachlorophenyl ester. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent must be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, using 6-aminopenicillanic acid, 7-aminocephalosporanic- acid and 7-amino-3-methylceph-3-em-4-carboxylic acid for the reaction in the free acid or salt form, aqueous solutions may be used for acylation with an acid halide or mixed anhydride under normal Schotten-Baumann conditions. The duration and temperature of the reactions are not critical. Temperatures in the range from −10° to 25° C. are commonly used for reaction times ranging from a few hours up to a day or more. The product may be isolated in any suitable way as the free acid or as a salt by appropriate adjustment of the pH. A preferred procedure is to extract the product in aqueous solution at a pH in the range from 2 to 2.5 with a suitable water-immiscible solvent such as ethyl acetate. In the case where the substituent $R_1$ is pyridyl the extraction is best accomplished in the range from 2.7 to 3.5. As an example of the isolation of the product, the reaction mixture can be evaporated to dryness and the residue treated with acetone to separate and remove any insoluble material. The acetone solution containing the product is then evaporated to give a second residue, which is dissolved in water and the aqueous solution is acidified to a pH in the range from about 2 to 2.5. This acidic solution is extracted with ethyl acetate and the ethyl acetate solution may be evaporated to give the product in the form of the free acid. Alternatively, the ethyl acetate solution may be treated with sodium or potassium 2-ethylhexanoate and the product usually precipitates; if not, the solution can then be concentrated to small volume and treated with ether to precipitate a carboxylate salt.

The N-(1,2-dihydro-2-oxonicotinyl)-2-phenylglycines and their reactive derivatives which are required as starting materials in the foregoing process can be prepared by methods illustrated in greater detail hereinafter. The silylated amino acid starting materials can be prepared by reacting the anhydrous 6-aminopenicillanic acid, 7-aminocephalosporanic acid or 7-amino-3- methylceph-3-em-4-carboxylic acid with a hexaalkyldisilazane. The preferred silylating agent is hexamethyldisilazane. Only the carboxyl group is silylated under the conditions used (e.g., 2-hour reflux in chloroform). After acylation, the silyl group is easily removed by treatment with water.

The free acids of the invention form carboxylate salts with any of a variety of inorganic and organic bases. Pharmaceutically-acceptable carboxylate salts are formed as indicated in the foregoing (e.g., with sodium or potassium 2-ethylhexanoate or by reacting the free acids with such bases as sodium hydroxide, sodium carbonate, sodium bicarbonate, potassium hydroxide, potassium carbonate, calcium carbonate, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention.

The compounds of the invention are new chemical compounds that are used as pharmacological agents and especially as broad spectrum antibacterial agents. They are active in vitro against strains of both gram-positive and gram-negative bacteria. Their activity in this regard is illustrated by that shown by N-[6-(2-cyclopentenylmethyl)-1,2-dihydro-2-oxonicotinyl]ampicillin, sodium salt. In an in vitro assay, the minimum inhibitory concentration of this compound of the invention against *Klebs. pneumoniae* MGH-1 was 6.3 micrograms/ml.; against *Ent. aerogenes* IMM-27 the minimum inhibitory concentration was 12.5 micrograms/ml.; and against *Pseudomonas aeruginosa* No. 733 the minimal inhibitory concentration was 6.3 microgram/ml.

The invention is illustrated by the following examples.

EXAMPLE 1

A solution of 0.5 g. of 1,1'-carbonyldiimidazole and 0.6 g. of 6-cyclopentylmethyl-1,2-dihydro-2-oxonicotinic acid in 5 cc. of N,N-dimethylacetamide is warmed at 50°–60° C. for approximately 1 hour until completion of carbon dioxide evolution. The solution is cooled and added to disilylated ampicillin solution prepared from a suspension of 2.87 millimoles of anhydrous sodium ampicillin in 50 cc. of tetrahydrofuran, treated with a solution of 0.7 cc. of trimethylsilyl chloride and 0.4 cc. of triethylamine with stirring at room temperature for 1 hour. After standing for 24 hours at room temperature the solution (reacted acylimidazolide and disilylated ampicillin) is poured into 200 cc. of cold water, hydrochloric acid is added to pH 2, and the mixture is extracted with ethyl acetate (three 50-cc portions). The ethyl acetate extracts are combined, washed with water and with saturated sodium chloride solution and finally dried with magnesium sulfate and filtered. A half-portion of the filtrate is evaporated to give a residue of the free acid, N-(6-cyclopentylmethyl-1,2-dihydro-2-oxonicotinyl)ampicillin. The remainder of the filtrate is treated with 0.45 cc. of a sodium 2-ethylhexanoate solution (50% w/v sodium 2-ethylhexanoate in butanol) and after about 10 minutes the product which separates is collected and dried over $P_2O_5$ in a desiccator under high vacuum. The product is N-(6-cyclopentylmethyl-1,2-dihydro-2-oxonicotinyl)ampicillin, sodium salt; $[\alpha]_D^{25}$ +156° (1.027%, pH 7 phophate buffer).

The corresponding potassium salt can be obtained in the foregoing general procedure by treating the dried ethyl acetate extracts with 1 ml. of a 50% solution of potassium 2-ethylhexanoate in butanol, concentrating the resulting mixture to a small volume and diluting with ether until precipitation of the product is complete. The potassium salt product is isolated by decantation of the liquid, washing with ether and drying under reduced pressure over anhydrous calcium sulfate.

EXAMPLE 2

6-(2-cyclopentenylmethyl)-1,2-dihydro-2-oxonicotinic acid (1.18 g.) and 1,1'-carbonyldiimidazole (0.86 g.) are warmed at 40° C. in 25 cc. of dry dimethylformamide for 90 minutes. The solution of the product 6-(2-cyclopentenylmethyl)-1,2-dihydro-2-oxonicotinylimidazolide is added to a solution of disilylated ampicillin prepared from 2 g. of sodium ampicillin, 1.44 cc. of trimethylsilyl chloride and 5.5 cc. of triethylamine in 100 cc. of dry tetrahydrofuran (the solution being stirred 1.5 hours at room temperature). The mixture is stirred for 20 hours at room temperature, cooled to 0° C. and added to a mixture of ice cold water (200 cc.) and ethyl acetate (100 cc.) at pH 6.95. The ethyl acetate layer is separated and discarded. The aqueous phase is cooled to 2° C., acidified with hydrochloric acid to pH 2.5, and extracted twice with 100-cc. portions of ethyl acetate. The organic layer is washed with 150 cc. of cold water, separated, dried with magnesium sulfate, and evaporated to dryness. The residual product is N-[6-(2-cyclopentenylmethyl)-1,2-dihydro-2-oxonicotinyl]ampicillin. To obtain the corresponding sodium salt, 3.4 g. of the free acid product is dissolved in 250 cc. of dry tetrahydrofuran and treated with 1.78 ml. of 50% (w/v) sodium 2-ethylhexanoate in butyl alcohol. Approximately 90 cc. of ether is added and the resulting precipitate is filtered off, washed with ether and dried over phosphorus pentoxide under high vacuum. The product is N-[6-(2-cyclopentenylmethyl)-1,2-dihydro-2-oxonicotinyl]ampicillin, sodium salt; $[\alpha]_D^{25}$ +136° (1.046% in pH 7 buffer).

EXAMPLE 3

Following the general procedure set forth in Example 1, 6-cyclohexyl-1,2-dihydro-2-oxonicotinic acid is converted to the activated imidazolide and the latter is reacted with disilylated ampicillin (from 1 g. of sodium ampicillin). The reaction mixture is worked up as in Example 1 to provide N-(6-cyclohexyl-1,2-dihydro-2-oxonicotinyl)ampicillin, sodium salt; $[\alpha]_D^{25}$ +169° (1.01% in methanol).

EXAMPLE 4

Triethylamine (1.26 g.) and trimethylsilyl chloride (1.3 g.) are added to a stirred suspension of 2 g. of ampicillin sodium salt in 75 cc. of tetrahydrofuran cooled in a cold water bath, and the mixture is stirred for 1.5 hours at room temperature. 6-Cyclohexylmethyl-1,2-dihydro-2-oxonicotinyl chloride (1.5 g.) is added and the mixture is stirred overnight and poured into water, acidified with hydrochloric acid to pH 2, extracted with ethyl acetate, and the ethyl acetate extracts washed with water, dried over magnesium sulfate and evaporated to dryness. The residual product, N-(6-cyclohexylmethyl)-1,2-dihydro-2-oxonicotinyl)ampicillin is dissolved in tetrahydrofuran, and the solution is filtered and treated with 1.9 cc. of sodium 2-ethylhexanoate solution (50% w/v in butyl alcohol). The crystalline product which separates, N-(6-cyclohexylmethyl)-1,2-dihydro-2-oxonicotinyl)ampicillin, sodium salt, is collected by filtration and dried; $[\alpha]_D^{25}$ +110° C. (1.025%, pH 7).

The oxonicotinyl chloride starting material for the above procedure can be prepared as follows: 6-Cyclohexylmethyl-1,2-dihydro-2-oxonicotinic acid (19.7 g.) is heated at steam bath temperature with 100 cc. of thionyl chloride for 50 minutes. The reaction solution is quickly cooled and poured into 500 cc. of hexane. The product, 6-cyclohexylmethyl-1,2-dihydro-2-oxonicotinyl chloride, is filtered off, washed with hexane and dried with constant high vacuum over phosphorus pentoxide; m.p. 161°–162° C.

EXAMPLE 5

Following the general procedure set forth in Example 1, 6-benzyl-1,2-dihydro-2-oxonicotinic acid (0.66 g.) is converted to the imidazolide in N,N-dimethylacetamide with 0.49 g. of 1,1'-carbonyldiimidazole and the imidazolide is reacted with 2.87 millimoles of bis-trimethylsilylampicillin in tetrahydrofuran. The free acid product of the reaction, N-(6-benzyl-1,2-dihydro-2-oxonicotinyl)ampicillin is isolated by evaporating the ethyl acetate extracts of the acidified reaction mixture. This product, dissolved in tetrahydrofuran, is converted to the sodium salt by treatment with 0.9 cc. of 50% w/v sodium 2-ethylhexanoate in butyl alcohol. The sodium salt is isolated by dilution with ether and filtration; $[\alpha]_D^{25}$ +136° (1.0% in methanol).

EXAMPLE 6

Following the general procedure set forth in Example 2, 6-phenethyl-1,2-dihydro-2-oxonicotinylimidazolide (prepared from 1.21 g. of 6-phenethyl-1,2-dihydro-2-oxonicotinic acid and 0.81 g. of 1,1'-carbonyldiimidazole in dimethylformamide) is reacted with disilylated ampicillin (2.23 g. triethylamine salt of ampicillin, 1.36 cc. of trimethylsilyl chloride and 3.06 cc. of triethylamine). The free acid product, N-(6-phenethyl-1,2-dihydro-2-oxonicotinyl)ampicillin, is isolated (3.4 g.) and converted to the triethylamine salt by dissolving it in 250 cc. of dry tetrahydrofuran containing a slight excess of triethylamine and precipitating the product with ether (ca. 700 cc.). The product, N-(6-phenethyl-1,2 dihydro-2-oxonicotinyl)ampicillin, triethylamine salt, is filtered off, washed with ether and dried over phosphorus pentoxide under high vacuum; $[\alpha]_D^{25}$ +92.3° (0.968% in pH 7).

The ampicillin triethylamine salt starting material can be prepared as follows: Ampicillin trihydrate (201.5 g.) is stirred as a suspension in acetonitrile (2.23 l.) and cooled to 1° C. To this stirred suspension 70 cc. of dry triethylamine is added rapidly and the suspension is stirred for 1 hour in an ice bath. The triethylamine product is filtered off, washed with 50 cc. of cold acetonitrile and with ether, and is finally dried under high vacuum; $[\alpha]_D^{25}$ +224° (1.03% in pH 7 buffer).

EXAMPLE 7

Following the procedure set forth in Example 1, bis-trimethylsilylampicillin (2.87 millimoles in 40 cc. of tetrahydrofuran) is reacted with 6-(1-adamantyl)-1,2-dihydro-2-oxonicotinyl imidazolide) prepared from the oxonicotinic acid, 0.75 g., in 10 cc. of dimethylformamide using 0.5 g. of 1,1'-carbonyldiimidazole). The product of the reaction after work-up is N-[6-(1-adamantyl)-1,2-dihydro-2-oxonicotinyl]ampicillin, sodium salt; $[\alpha]_D^{25}$ +129° (1% in pH 7).

EXAMPLE 8

A solution of 6-(o-methoxybenzyl)-1,2-dihydro-2-oxonicotinylimidazolide (prepared by the reaction of 8.56 g. of the oxonicotinic acid with 5.35 g. of 1,1'-carbonyldiimidazole heated at 40°–50° C. in 100 cc. of dimethylformamide solution for 1.5 hours) is added to a solution of bis-trimethylsilylampicillin (prepared from a suspension of 14.88 g. of ampicillin triethylamine salt in 250 cc. of tetrahydrofuran by adding 8.9 cc. of trimethylsilyl chloride and 4.62 cc. of tiethylamine with cooling and stirring at room temperature for 1 hour). The reaction mixture is stirred overnight at room temperature, diluted with 100 cc. of ice water, extracted with ethyl acetate at pH 7 and the aqueous phase worked up by a procedure similar to that of Example 2 for the isolation of the free acid. The free acid product is N-[6-(o-methoxybenzyl)-1,2-dihydro-2-oxonicotinyl]ampicillin. To obtain the triethylamine salt, the free acid is dissolved in tetrahydrofuran, and the solution is treated with an equivalent of triethylamine and the salt precipitated with ether. The collected product, N-[6-(o-methoxybenzyl)-1,2-dihydro,-2-oxonicotinyl]ampicillin, triethylamine salt, is dried over phosphorus pentoxide; $[\alpha]_D^{25}$ +133° (1% in methanol).

The triethylamine salt is converted to the corresponding sodium salt by dissolving in 800 cc. of water, acidifying to pH 2 and extracting twice with 300-cc. portions of ethylacetate. The dried ethyl acetate extract is treated with 9.4 cc. of sodium 2-ethylhexanoate solution (50% w/v in butyl alcohol) and the sodium salt is collected and vacuum dried over phosphorus pentoxide; $[\alpha]_D^{25}$ +134° (1.01% in methanol).

EXAMPLE 9

Following a procedure similar to that set forth in Example 8, 6-(m-methoxybenzyl)-1,2-dihydro-2-oxonicotinylimidazolide (prepared from 1.4 g. of 6-(m-methoxybenzyl)-1,2-dihydro-2-oxonicotinic acid and 0.86 g. of 1,1'-carbonyldiimidazole) and bis-trimethylsilylampicillin (prepared from 2 g. of sodium ampicillin, 1.44 cc. of trimethylsilyl chloride and 5.45 cc. of triethylamine) are reacted and the reaction mixture worked up to obtain the free acid product, N-[6-(m-methoxybenzyl)-1,2-dihydro-2-oxonicotinyl]ampicillin. To obtain the sodium salt, the free acid is dissolved in tetrahydrofuran and treated wth 1.79 cc. of sodium 2-ethylhexanoate (50% w/v in butanol). Ether is added and the product is collected and dried. The product is N-[6-(m-methoxybenzyl)-1,2-dihydro-2-oxonicotinyl]-ampicillin, sodium salt; $[\alpha]_D^{25}$ +75° (1.03% in pH 7 buffer).

EXAMPLE 10

Following a procedure similar to that set forth in Example 8, 6-(p-methoxybenzyl)-1,2-dihydro-2-oxonicotinylimidazolide (prepared from 6-(p-methoxybenzyl)-1,2-dihydro-2-oxonicotinic acid, 1.4 g., and 1,1'-carbonyldiimidazole, 0.86 g.) and bis-triemethylsilylampicillin (prepared from sodium ampicillin, 2.0 g., trimethylsilyl chloride, 1.44 cc., and triethylamine, 5.45 cc.) are reacted and the reaction mixture worked up to obtain the free acid product, N-[6-(p-methoxybenzyl)-1,2-dihydro-2-oxonicotinyl]ampicillin. The product obtained by treating the free acid (3.5 g.) with an equivalent of triethylamine and working up the ether-precipitated salt is N-[6-(p-methoxybenzyl)-1,2- dihydro-2-oxonicotinyl]ampicillin, triethylamine salt; $[\alpha]_D^{25}$ +123° (1% in methanol).

EXAMPLE 11

Following the procedure set forth in Example 1, a solution of 6(p-chlorobenzyl)-1,2-dihydro-2-oxonicotinylimidazolide (prepared by warming at 40°–50° C. for 1 hour a solution of 0.72 g. of 6-(p-chlorobenzyl)-1,2-dihydro-2-oxonicotinic acid and 0.5 g. 1,1'-carbonyldiimidazole in 6 cc. dimethylformamide) is added to a solution of bis-trimethylsilylampicillin (prepared from 2.87 millimoles of sodium ampicillin, 0.7 cc. of trimethylsilyl chloride, 0.4 cc. of triethylamine in 30 cc. of tetrahydrofuran). The reaction mixture is stirred for 24 hours at room temperature and worked up by a procedure similar to that of Example 1, to obtain the product N-[6-(p-chlorobenzyl)-1,2-dihydro-2-oxonicotinyl]ampicillin, sodium salt; $[\alpha]_D^{25}$ +156° (1.02% in methanol).

EXAMPLE 12

A cooled solution of the imidazolide of 6-(p-hydroxybenzyl)-1,2-dihydro-2-oxonicotinic acid (prepared from 8.66 g. of the acid and 6.08 g. of 1,1'-carbonyldiimidazole in 66.5 cc. of dimethylformamide heated at 45°–52° for 1 hour) is added to a solution of bis-trimethylsilylampicillin (prepared from 18 g. of ampicillin triethylamine salt, 13.3 cc. of trimethylsilyl chloride and 5.25 cc. of triethylamine in 150 cc. of tetrahydrofuran). The reaction mixture is stirred 4 hours at room temperature and is then diluted with 500 cc. of ice water (pH 6.2) and 500 cc. of ethyl acetate. The ethyl acetate is separated and discarded. An additional 500 cc. of ethyl acetate is added to the aqueous layer and with stirring the mixture is acidified to pH 2 with hydrochloric acid. The ethyl acetate is separated and the extraction repeated with another 500-cc. portion of ethyl acetate. The combined ethyl acetate layers after washing with water are dried with magnesium sulfate, filtered and sodium 2-ethylhexanoate solution (12.5 cc., 50% w/v in butanol) is added to the filtrate with stirring. The solid product which separates is collected by filtration, redissolved in water, and the solution adjusted to pH 2 and extracted with ethyl acetate. The extracts are dried and evaporated to provide the product N-[6-(p-hydroxybenzyl)-1,2-dihydro-2-oxonicotinyl]ampicillin, sodium salt; $[\alpha]_D^{25}$ +107° (1.035% in methanol).

The triethylamine salt is obtained by treating the sodium salt product with triethylamine; $[\alpha]_D^{25}$ +109° (0.99% in methanol).

EXAMPLE 13

A solution of bis-trimethylsilylampicillin (2.87 millimoles in tetrahydrofuran) is combined with a cooled solution of 6-benzyl-1,2-dihydro-1-methyl-2-oxonicotinyl imidazolide (prepared from 0.68 g. of 6-benzyl-1,2-dihydro-1-methyl-2-oxonicotinic acid, 0.5 g. 1,1'-carbonyldiimidazole in 5 cc. of dimethylformamide at 50°–60° for 0.5 hour). The reaction mixture is stirred for 24 hours at room temperature and worked up using a procedure similar to that used in Example 1, to obtain the product N-(6-benzyl-1,2-dihydro-1-methyl-2-oxonicotinyl)ampicillin, sodium salt; $[\alpha]_D^{25}$ +163° (1.04% in methanol).

EXAMPLE 14

A solution of imidazolide (prepared from 0.65 g. of 2,5,5a,6,7,8,9,9a-octahydro-2-oxo-1-H-indeno[1,2-b]pyridine-3-carboxylic acid and 0.5 g. of 1,1'-carbonyldiimidazole warmed in 10 cc. of dimethylformamide for 45 minutes) is added to a solution of bis-trimethylsilylampicillin (prepared from 2.87 millimoles of sodium ampicillin, 0.7 cc. of trimethylsilyl chloride and 0.4 cc. of triethylamine in 30 cc. of tetrahydrofuran).

The reaction mixture is stirred at room temperature for 22 hours, poured into water, and the pH adjusted with hydrochloric acid to 2.5. The aqueous mixture is extracted thoroughly with ethyl acetate, and the extracts are washed with water and saturated salt solution and are dried with magnesium sulfate and filtered. Sodium 2-ethylhexanoate (0.9 g., 50% w/v in butyl alcohol) is added to the filtrate and the product, N-(2,5,5a,6,7,8,9,9a-octahydro-2-oxo-1H-indeno[1,2-b]pyridinecarbonyl)ampicillin, sodium salt, is collected, washed with ether and dried over phosphorus pentoxide under high vacuum; $[\alpha]_D^{25}$ +147° (1.01% in pH 7 buffer).

EXAMPLE 15

A cooled solution of imidazolide (prepared from 0.65 g. of cis-2,4b,5,6,7,8,8a,9-octahydro-2-oxo-1H-indeno[2,1-b]pyridine-3-carboxylic acid, 0.5 g. of 1,1'-carbonyldiimidazole in 10 cc. of dimethylformamide heated at 50°–60° for 1 hour) is added to a suspension of bis-trimethylsilylampicillin (prepared from 2.87 millimoles of sodium ampicillin, 0.7 cc. of trimethylsilyl chloride and 0.4 cc. of triethylamine in 40 cc. of tetrahydrofuran). The mixture is reacted and worked up in the same way described in Example 14 to provide the product, N-(cis-2,4b,5,6,7,8,8a,9-octahydro-2-oxo-1H-indeno[2,1-b]pyridine-3-carbonyl)ampicillin, sodium salt; $[\alpha]_D^{25}$ +164° (1.02% in pH 7 buffer).

EXAMPLE 16

Using the same procedure as in Example 15, 6-furfuryl-1,2-dihydro-2-oxonicotinylimidazolide and disilylated ampicillin are reacted and worked up to provide the product, N-(6-furfuryl-1,2-dihydro-2-oxonicotinyl)ampicillin, sodium salt; $[\alpha]_D^{25}$ +158° (1.025% in pH 7 buffer).

EXAMPLE 17

Using the same procedure as in Example 14, 0.65 g. of 6-(2-thenyl)-1,2-dihydro-2-oxonicotinic acid is converted to the imidazolide and the latter is reacted with disilylated ampicillin. The reaction mixture is worked up in the same manner to provide the product, N-[6-(2-thenyl)-1,2-dihydro-2-oxonicotinyl]ampicillin, sodium salt; $[\alpha]_D^{25}$ +146° (1.04% in methanol).

EXAMPLE 18

A cooled solution of imidazolide (prepared from 6-(2-pyridyl)-1,2-dihydro-2-oxonicotinic acid (1.08 g.) heated in 50 cc. of dry dimethylformamide with 0.81 g. of 1,1'-carbonyldiimidazole at 45° C. for 2 hours) is added to a suspension of bis-trimethylsilylampicillin (prepared from 2.25 g. triethylamine salt of ampicillin, 1.34 cc. of trimethylsilyl chloride and 5.06 cc. of 10% w/v triethylamine solution in dry tetrahydrofuran stirred at room temperature in 50 cc. of dry tetrahydrofuran for several hours). The reaction mixture is stirred at room temperature for 18 hours, ice water (200 cc.)

is added, and the solution (pH 6.8) is extracted with 100 cc. of ethyl acetate. The organic layer is discarded and the aqueous layer is cooled to 5°C., acidified to pH 3 with hydrochloric acid and extracted with 100 cc. of ethylacetate. The ethylacetate extraction is repeated five times with fresh 100-cc. portions. The collected organic layers are dried with magnesium sulfate, filtered, and the filtrate is treated with 1.66 cc. of 50% w/v sodium 2-ethylhexanoate (solution in butanol). The product, N-[6-(2-pyridyl)-1,2-dihydro-2-oxonicotinyl]ampicillin, sodium salt, is precipitated with ether, filtered off and vacuum dried over phosphorus pentoxide; $[\alpha]_D^{25}$ +196° (1.03 in pH 7 buffer). The corresponding free acid, N-[6-(2-pyridyl)-1,2-dihydro-2-oxonicotinyl]ampicillin, is obtained by dissolving the sodium salt in a mixture of ice water and ethylacetate and acidifying to pH 2.7. The solid free acid which separates is collected, washed with water and vacuum dried over phosphorus pentoxide.

EXAMPLE 19

A cooled solution of 6-(3-pyridyl)-1,2-dihydro-2-oxonicotinylimidazolide (prepared from 21.62 g. of the corresponding acid heated at 55°–60° C. for 1.5 hours with 16.22 g. of 1,1'-carbonyldiimidazole in 430 cc. of dimethylformamide) is added to a solution of bis-trimethylsilylampicillin (prepared by treating 48.3 g. of ampicillin triethylamine salt in 372 cc. of tetrahydrofuran with 27.1 cc. of trimethylsilyl chloride and 14 cc. of triethylamine with cooling and stirring for 30 minutes). The reaction mixture is stirred at room temperature for 3 hours and is cooled and diluted with 1.27 liters of water. The aqueous mixture is extracted with 750 cc. of ethyl acetate (the organic layer is discarded) and the aqueous layer is cooled, acidified to pH 2.7 and extracted with 750 cc. of ethyl acetate. The separated aqueous layer is extracted successively three times with 500-cc. portions of fresh ethyl acetate. The combined ethyl acetate extracts are diluted with 2.75 liters of ether and set at 0° C. overnight. The product, N-[6-(3-pyridyl)-1,2-dihydro-2-oxonicotinyl]ampicillin, is collected and washed with ether. To obtain the sodium salt, the product is dissolved in 1.9 liters of dioxane and filtered, 33.6 cc. of 50% w/v sodium 2-ethylhexanoate (in butyl alcohol) is added to the filtrate, and the product which separates, N-[6-(3-pyridyl)-1,2-dihydro-2-oxonicotinyl]ampicillin, sodium salt, is collected by filtration and vacuum dried over phosphorus pentoxide.

The sodium salt is converted to the free acid by dissolving in a mixture of 1 liter of ice cold water and 400 cc. of ethyl acetate and acidifying to pH 2.7 with stirring. The free acid is collected by filtration, washed with water and vacuum dried over phosphorus pentoxide; $[\alpha]_D^{25}$ +199° (1.035% in pH 7 buffer.) To obtain the sodium salt in purified form the free acid product is dissolved in 235 cc. of 75% isopropanol-25% water solution and in turn 14.27 cc. of 50% w/v sodium 2-ethylhexanoate (in butanol) and 1.2 liters of pure isopropanol are added. The solution is chilled. The crystalline sodium salt of N-[6-(3-pyridyl)-1,2-dihydro-2-oxonicotinyl]ampicillin, which separates in crystalline form upon scratching, is collected by filtration, washed with isopropanol and with ether and is dried over phosphorus pentoxide with high vacuum; $[\alpha]_D^{25}$ +183° (1% in pH 7 buffer).

EXAMPLE 20

A cooled solution of 6-(4-pyridyl)-1,2-dihydro-2-oxonicotinylimidazolide (prepared from 1.08 g. of the corresponding oxonicotinic acid and 0.81 g. of 1,1'-carbonyldiimidazole in 100 cc. of dimethylformamide) is added to a solution of bis-trimethylsilylampicillin (prepared by treating 2.25 g. of triethylamine salt of ampicillin in 50 cc. of dry tetrahydrofuran with 1.34 cc. trimethylsilyl chloride and 5 cc. of triethylamine). The reaction is allowed to proceed for 20 hours, and is diluted with 200 cc. of ice water and extracted at pH 7 with 100 cc. of ethyl acetate. The organic layer is discarded, and the aqueous layer is acidified to pH 3 and extracted four times successively with 100-cc. portions of ethyl acetate. The combined ethyl acetate extracts are washed with 150 cc. of water, dried with magnesium sulfate, filtered and evaporated to dryness under vacuum. The residual product is N-[6-(4-pyridyl)-1,2-dihydro-2-oxonicotinyl]ampicillin. The residue is dissolved in a minimum of tetrahydrofuran, treated with 1.66 cc. of 50% w/v sodium 2-ethylhexanoate (in butanol), and the sodium salt is precipitated with ether. The product, N-[6-(4-pyridyl)-1,2-dihydro-2-oxonicotinyl]ampicillin, sodium salt, is collected by filtration and dried over phosphorus pentoxide under high vacuum $[\alpha]_D^{25}$ +136° (1.02% in pH 7 buffer).

EXAMPLE 21

A cooled solution prepared by reacting 6-(2-furyl)-1,2-dihydro-2-oxonicotinic acid (1.02 g.) and 1,1'-carbonyldiimidazole (0.81 g.) at 50° for 90 minutes in 25 cc. of dimethylformamide is added to a solution of bis-dimethylsilylampicillin (prepared from 2.25 g. of ampicillin triethylamine salt, 1.34 cc. of trimethylsilyl chloride, 0.506 g. of triethylamine in 50 cc. of dry tetrahydrofuran). The resultant mixture is stirred 21 hours, diluted with 200 cc. of ice water, cooled and extracted with 100 cc. of ethyl acetate. The organic layer is discarded. The aqueous layer is acidified to pH 2 and extracted successively with four 100-cc. portions of ethyl acetate. The combined ethyl acetate extracts are washed with 100 cc. of water, separated and the organic layer dried with magnesium sulfate. The tethyl acetate solution is filtered and evaporated to dryness under reduced pressure (under 30° C.). The residual product is N-[6-(2-furyl)-1,2-dihydro-2-oxonicotinyl]ampicillin. The product is dissolved in a minimum of tetrahydrofuran, 0.7 cc. of triethylamine is added and the salt precipitated with ether. The product, N-[6-(2-furyl)-1,2-dihydro-2-oxonicotinyl]ampicillin, triethylamine salt, is isolated by decanting and drying; $[\alpha]_D^{25}$ +106° (1.0%, in pH 7 buffer).

EXAMPLE 22

A mixture of 6-(2-thienyl)-1,2-dihydro-2-oxonicotinic acid (11 g.) in 83 cc. of N,N-dimethylacetamide is heated with 8 g. of 1,1'-carbonyldiimidazole at 55° C. until gas evolution ceases (approximately 1 hour). The reaction mixture is cooled and added to a solution of disilyated ampicillin (from 22.5 g. of ampicillin triethylamine salt, 13 g. of trimethylsilyl chloride and 7 cc. of triethylamine in 200 cc. of tetrahydrofuran). This mixture is stirred at room temperature for 3.3 hours. Cold water (600 cc.) and ethyl acetate (500 cc.) are added and after shaking, the layers are separated and the ethyl acetate solution discarded. The aqueous layer is covered with a fresh 500-cc. portion of ethyl acetate and, while mechanically stirring the mixture, hydrochloric acid is added to pH 2. The mixture is filtered and the filtrate layers separated. The aqueous layer is extracted with 250 cc. of ethyl acetate, and the combined ethyl acetate extracts are washed with 100 cc. of water and dried over magnesium sulfate and filtered. The filtrate, containing N-[6-(2-thienyl)-1,2-dihydro-2-oxonicotinyl]ampicillin, is mixed with 5 cc. of triethylamine and the mixture is cooled overnight. The resulting product, N[-6-(2-thienyl)-1,2-dihydro-2-oxonicotinyl]ampicillin, triethylamine salt, is separated by decantation and filtration; $[\alpha]_D^{25}$ +124° (1% in methanol). To obtain a second crop of the salt product, the filtrate is poured into 1.5 liters of ether and the precipitate is collected and dried over phorphorus pentoxide in high vacuum; $[\alpha]_D^{25}$ +134° (1% in methanol). To obtain the corresponding sodium salt, this last crop is dissolved in 37.5 cc. of 1:1 tetrahydrofuran-acetonitrile and treated with 1.25 cc. of 50% sodium 2-ethylhexanoate (in butanol) dissolved in 10 cc. of the same mixed solvent. The product, N-[6-(2-thienyl)-1,2-dihydro-2-oxonicotinyl]ampicillin, sodium salt, is filtered off and dried under vacuum; $[\alpha]_D^{25}$ +154° (1.02% in methanol).

EXAMPLE 23 a. Cephalexin hydrate (1.05 g.) is suspended in 10 cc. of water and with mechanical stirring in an ice bath the pH is carefully adjusted to 9.1 with 1 normal sodium hydroxide. Potassium bicarbonate (0.6 g.) is added to approximately pH 8 and in turn tetrahydrofuran (10 cc.) and 6-cyclohexylmethyl-1,2-dihydro-2-oxonicotinyl chloride (0.72 g.) dissolved in 10 cc. of tetrahydrofuran are added. This mixture is stirred for 1 hour in the ice bath, diluted with 25 cc. of water and adjusted with dilute hydrochloric acid to pH 7. The reaction mixture is filtered and the filtrate adjusted to pH 2 with one normal hyrochloric acid. The suspension is extracted twice with successive equal volumes of ethyl acetate, the organic layers are separated, dried over magnesium sulfate, filtered and the filtrate evaporated to dryness. The residual product is N-(6-cyclohexylmethyl-1,2-dihydro-2-oxonicotinyl)cephalexin. The product is taken up with 25 cc. of ethyl acetate, filtered, and excess triethylamine is added dropwise. The product, N-(6 -cyclohexylmethyl-1,2-dihydro-2-oxonicotinyl)-cephalexin, triethylamine salt, is collected by filtration and dried over phosphorus pentoxide under vacuum; $[\alpha]_D^{25}$ +55.7° (0.834% in 20% methanol, pH 7 buffer).

b. To obtain the free acid, N-(6-cyclohexylmethyl-1,2-dihydro-2-oxonicotinyl)cephaloglycin and its triethylamine salt, the procedure of paragraph (a) is followed substituting an equivalent amount of cephaloglycin dihydrate for cephalexin.

STARTING MATERIALS:

The 6-substituted-1,2-dihydro-2-oxonicotinic acid starting materials for the foregoing examples and a number of their precursor 6-substituted-1,2-dihydro-2-oxonicotinonitriles are novel substances. The preparation of these substances is described in the next following examples.

A. 6-Substituted-1,2-Dihydro-2-Oxonicotinonitriles 1. 6-Cyclopentylmethyl-1,2-dihydro-2-oxonicotinonitrile; a mixture of 26.5 g. of cyclopentyl-2-propanone and 21 g. of ethyl formate is added dropwise with cooling to a stirred mixture of 18.2 g. of a 57% sodium hydride dispersion in mineral oil and 250 ml. of benzene. The resulting thick suspension is stirred at room temperature for 20 hours and is then treated with 100 ml. of water. The aqueous phase is separated and the organic phase extracted with water. The combined aqueous phase and aqueous extract is washed with ether. To the resulting aqueous solution, containing the sodium salt of 4-cyclopentylacetoacetaldehyde, is added 17 g. of 2-cyanoacetamide, 6 g. of glacial acetic acid and a solution of piperidine acetate prepared from 5 g. of glacial acetic acid, 10 ml. of water and enough piperidine to give a basic reaction to litmus. The resulting solution is heated at reflux for 4 hours, cooled and acidified with acetic acid. The product which separates, 6-cyclopentylmethyl-1,2-dihydro-2-oxonicotinonitrile, is collected by filtration and washed with ether; m.p. 135°–140° C. after crystallization from ethyl acetate.

In a similar manner, the following nitriles are prepared.

2. 6-(2-Cyclopentenylmethyl)-1,2-dihydro-2-oxonicotinonitrile; from a solution of the sodium salt of 4-(2-cyclopentenyl)acetoacetaldehyde (in 100 ml. of water, prepared from 20 g. of a 55% sodium hydride dispersion in mineral oil, 250 ml. of benzene, 25 g. of (2-cyclopentenyl)-2-propanone and 21 g. of ethyl formate), 15 g. of glacial acetic acid, 5 ml. of piperidine and 17 g. of 2-cyanoacetamide; m.p. 140°–143.5° C. after washing with ether.

3. 6-Cyclohexyl-1,2-dihydro-2-oxonicotinonitrile; from a solution of the sodium salt of β-oxocyclohexanepropionaldehyde (in 100 ml. of water, prepared from 17 g. of a 57% sodium hydride dispersion in mineral oil, 350 ml. of benzene, 25 g. of cyclohexyl methyl ketone and 21.5 g. of ethyl formate), 17 g. of 2-cyanoacetamide, 14 ml. of glacial acetic acid and 4 ml. of piperidine; m.p. 213°–215° C. after crystallization from acetonitrile.

4. 6-Cyclohexylmethyl-1,2-dihydro-2-oxonicotinonitrile; from a solution of the sodium salt of 4-cyclohexylacetoacetaldehyde (in 355 ml. of water, prepared from 31.9 g. of a 57% sodium hydride dispersion in mineral oil, 1 l. of benzene, 100 g. of cyclohexyl-2-propanone and 57.7 g. of ethyl formate), 60.5 g. of 2-cyanoacetamide and a solution of 16.5 ml. of piperidine and 8.5 ml. of glacial acetic acid in 21 ml. of water; m.p. 179°–180° C. after crystallization from acetonitrile and from ethanol.

5. 6-Benzyl-1,2-dihydro-2-oxonicotinonitrile; from a solution of the sodium salt of 4-phenylacetoacetaldehyde (in 700 ml. of water, prepared from 63 g. of a 57% sodium hydride dispersion in mineral oil, 2 l. of benzene, 100 g. of phenyl-2-propanone and 79.5 g. of ethyl formate), 63 g. of 2-cyanoacetamide and a solution of 18 ml. of piperidine and 9.5 ml. of glacial acetic acid in 25 ml. of water; m.p. 190°–197° C. after crystallization from methanol.

6. 6-Phenethyl-1,2-dihydro-2-oxonicotinonitrile (J. Org. Chem. 30, 3596 (1965).

7. 6-(1-Adamantyl)-1,2-dihydro-2-oxonicotinonitrile; from a solution of the sodium salt of β-oxo-1-adamantanepropionaldehyde (in 100 ml. of water, prepared from 12.1 g. of a 50% sodium hydride dispersion in mineral oil 350 ml. of benzene, 24.8 g. of 1-adamantyl methyl ketone and 21.5 g. of ethyl formate), 12.1 g. of 2-cyanoacetamide and a solution of 15 g. of glacial acetic acid and 5 ml. of piperidine in 20 ml. of water; m.p. 309°–311° C. after crystallization from glacial acetic acid.

8. 6-(o-Methoxybenzyl)-1,2-dihydro-2-oxonicotinonitrile; from a solution of the sodium salt of 4-(o-methoxypehnyl)acetoacetaldehyde (in 300 ml. of water, prepared from 28.4 g. of a 55% sodium hydride dispersion in mineral oil, 620 ml. of benzene, 100.2 g. of o-methoxyphenyl-2-propanone and 46 g. of ethyl formate), 52.1 g. of 2-cyanoacetamide, and a solution of 7 ml. of glacial acetic acid and 12 ml. of piperidine in 17 ml. of water; m.p. 191°–195° C. after crystallization from ethanol.

9. 6-(m-Methoxybenzyl)-1,2-dihydro-6-oxonicotinonitrile; m.p. 175°–178° C. after crystallization from ethanol.

10. 6-(p-Methoxybenzyl)-1,2-dihydro-6-oxonicotinonitrile; m.p. 196°–198° C.

11. 6-(p-Chlorobenzyl)-1,2-dihydro-2-oxonicotinonitrile; from a solution of the sodium salt of 4-(p-chlorophenyl)acetoacetaldehyde (in 100 ml. of water, prepared from 9.1 g. of a 57% sodium hydride dispersion in mineral oil 200 ml. of benzene, 19.9 g. of p-chlorophenyl-2-propanone and 13.2 g. of ethyl formate), 9.0 g. of 2-cyanoacetamide, 4 ml. of glacial acetic acid and a solution of piperidine acetate prepared from 2.5 ml. of glacial acetic acid, 5 ml. of water and enough piperidine to render the solution basic to litmus; m.p. 205°–210° C. after crystallization from acetonitrile.

12. 2,5,5a,6,7,8,9,9a-Octahydro-2-oxo-1H-indeno[1,2-b]pyridine-3-carbonitrile; from a solution of the sodium salt of hexahydro-1-oxo-2-indancarboxaldehyde (in 100 ml. of water, prepared from 12 g. of a 57% sodium hydride dispersion in mineral oil, 250 ml. of benzene, 18.6 g. of hexahydro-1-indanone and 14.8 g. of ethyl formate), 12 g. of 2-cyanoacetamide, and a solution of 11 g. of glacial acetic acid and 2 g. of piperidine in 20 ml. of water; m.p. 212°–215.5° C. after crystallization from ethanol.

13. cis-2,4b,5,6,7,8,8a,9-Octahydro-2-oxo-1H-indeno[2,1-b]pyridine-3-carbonitrile; from a solution of the sodium salt of hexahydro-2-oxo-1-indancarboxaldehyde (in 100 ml. of water, prepared from 10.1 g. of a sodium hydride dispersion in mineral oil, 200 ml. of benzene, 16.1 g. of hexahydro-2-indanone and 17.2 g. of ethyl formate), 10 g. of 2-cyanoacetamide, and a solution of piperidine acetate prepared from 3.5 ml. of glacial acetic acid, 10 ml. of water and enough piperidine to render the solution basic to litmus; m.p. 244°–246° C. after crystallization from methanol.

14. 6-Furfuryl-1,2-dihydro-2-oxonicotinonitrile; from a solution of the sodium salt of 4-(2-furyl)acetoacetaldehyde (in 100 ml. of water, prepared from 13.7 g. of a 57% sodium hydride dispersion in mineral oil, 350 ml. of benzene, 13.7 g. of (2-furyl)-2-propanone and 20.3 g. of ethyl formate), 13.6 g. of 2-cyanoacetamide, and a solution of piperidine acetate prepared from 2 g. of glacial acetic acid, 10 ml. of water and enough piperidine to render the solution basic to litmus.

15. 6-(2-Thenyl-1,2-dihydro-2-oxonicotinonitrile; from a solution of the sodium salt of 4-(2-thienyl)acetoacetaldehyde (in 100 ml. of water, prepared from 13.7 g. of a 57% sodium hydride dispersion in mineral oil, 350 ml. of benzene, 20 g. of (2-thienyl)-2-propanone and 20.3 g. of ethyl formate), 12 g. of 2-cyanoacetamide, 11 g. of glacial acetic acid and 3 g. of piperidine.

16. 6-(2-Pyridyl)-1,2-dihydro-2-oxonicotinonitrile; to a cold slurry of 28.4 g. of sodium methoxide in 500 ml. of tetrahydrofuran is added dropwise, with stirring, a mixture of 60.6 g. of methyl 2-pyridyl ketone and 37.0 g. of ethyl formate. The resulting suspension is stirred at room temperature for 44 hours and the precipitated sodium salt of β-oxo-2-pyridine-propionaldehyde is collected by filtration. This salt is dissolved in 150 ml. of water and the solution is treated with 42 g. of 2-cyanoacetamide and with a solution of piperidine acetate prepared from 4.2 ml. of glacial acetic acid, 11 ml. of water and enough piperidine to render the solution basic to litmus. The resulting mixture is heated at reflux for 3 hours, treated with activated charcoal and filtered. The filtrate is acidified with acetic acid and cooled. The nitrile product is collected by filtration and dried; m.p. 237°–239° C. (dec.) after trituration with ethanol.

17. 6-(3-Pyridyl)-1,2-dihydro-2-oxonicotinonitrile; m.p. 285°–289° C. (dec.) after trituration with ethanol.

18. 6-(4-Pyridyl)-1,2-dihydro-2-oxonicotinonitrile; m.p. >350° C. after trituration with ethanol.

19. 6-(2-Furyl)-1,2-dihydro-2-oxonicotinonitrile; m.p. 140°–145° C. after crystallization from aqueous ethanol.

20. 6-(2-Thienyl)-1,2-dihydro-2-oxonicotinonitrile; m.p. 127°–128° C. after two crystallizations from aqueous ethanol.

21. 6-Benzyl-1,2-dihydro-1-methyl-2-oxonicotinonitrile; a mixture of 10.5 g. of 6-benzyl-1,2-dihydro-2-oxonicotinonitrile, 3.6 g. of potassium hydroxide, 4.7 ml. of iodomethane and 50 ml. of ethanol is stirred and heated at reflux for 2 hours. An additional 3.1 ml. of iodomethane is added and stirring and heating at reflux are continued for 3 hours. The mixture is evaporated at reduced pressure and the residue washed with warm water and extracted with two 50-ml. portions of chloroform. The combined chloroform extracts are washed with water, dried and evaporated. The residual oil is dissolved in 25 ml. of hot glacial acetic acid and the solution is chilled to crystallize 6-benzyl-1,2-dihydro-1-methyl-2-oxonicotinonitrile which is removed by filtration, washed with ethyl acetate and dried; m.p. 110°–111.5° C. after trituration with aqueous sodium hydroxide, washing with water and drying.

B. 6-Substituted-1,2-Dihydro-2-Oxonicotinic Acids 1. 6-Cyclopentylmethyl-1,2-dihydro-2-oxonicotinic acid; a mixture of 5 g. of 6-cyclopentylmethyl-1,2-dihydro-2-oxonicotinonitrile and 50 g. of 20% aqueous sodium hydroxide is heated at reflux for 24 hours. The hot solution is filtered into an excess of well-stirred hydrochloric acid ice mixture. The precipitate of 6-cyclopentylmethyl-1,2-dihydro-2-oxonicotinic acid is collected by filtration, washed with water and dried; m.p. 153°–158° C. after crystallization from ethyl acetate.

In a similar manner the following acids are prepared by alkaline hydrolysis of the corresponding nitrile and by acidification.

2. 6-(2-Cyclopentenylmethyl)-1,2-dihydro-2-oxonicotinic acid; m.p. 196°–197.5° C. from 95% ethanol.

3. 6-Cyclohexyl-1,2-dihydro-2-oxonicotinic acid; m.p. 228°–232° C. from 95% ethanol.

4. 6-Cyclohexylmethyl-1,2-dihydro-2-oxonicotinic acid; m.p. 186°–187° C. from aqueous acetonitrile.

5. 6-Benzyl-1,2-dihydro-2-oxonicotinic acid; m.p. 195°–200° C. (dec.) from 95% ethanol.

6. 6-Phenethyl-1,2-dihydro-2-oxonicotinic acid; m.p. 220°–221° C. after crystallization from acetic acid.

7. 6-(1-Adamantyl)-1,2-dihydro-2-oxonicotinic acid; m.p. 313°–314° C. from acetic acid.

8. 6-(o-Methoxybenzyl)-1,2-dihydro-2-oxonicotinic acid; m.p. 201°–202° C. from 95% ethanol.

9. 6-(m-Methoxybenzyl)-1,2-dihydro-2-oxonicotinic acid; m.p. 214°–215° C. from 95% ethanol.

10. 6-(p-Methoxybenzyl)-1,2-dihydro-2-oxonicotinic acid; m.p. 192°–194° C. from 95% ethanol.

11. 6-(p-Chlorobenzyl)-1,2-dihydro-2-oxonicotinic acid; m.p. 216°–223° C. (dec.) from 95% ethanol.

12. 6-Benzyl-1,2-dihydro-1-methyl-2-oxonicotinic acid; m.p. 159°–160° C. from ethanol.

13. 2,5,5a,6,7,8,9a-Octahydro-2-oxo-1H-indeno[1,2-b]pyridene-3-carboxylic acid; m.p. 226°–228° C. (dec.) from ethanol.

14. cis-2,4b,5,6,7,8,8a,9-Octahydro-2-oxo-1H-indeno[2,1-b]pyridine-3-carboxylic acid; m.p. 216°–230° C. from ethanol.

15. 6-Furfuryl-1,2-dihydro-2-oxonicotinic acid; m.p. 200°–203° C. (dec.) from 95% ethanol.

16. 6-(2-Thenyl)-1,2-dihydro-2-oxonicotinic acid; m.p. 175°–178° C. (dec.) from 60% ethanol.

17. 6-(2-Pyridyl)-1,2-dihydro-2-oxonicotinic acid; m.p. 299°–300° C. (dec.) from dimethyl sulfoxide.

18. 6-(3-Pyridyl)-1,2-dihydro-2-oxonicotinic acid; m.p. 295°–296° C. (dec.) from dimethyl sulfoxide-ethanol.

19. 6-(4-Pyridyl)-1,2-dihydro-2-oxonicotinic acid; m.p. 311°–312° C. (dec.) from aqueous dimethyl sulfoxide.

20. 6-(2-Furyl)-1,2-dihydro-2-oxonicotinic acid; m.p. 226°–230° C. (dec.)

21. 6-(2-Thienyl)-1,2-dihydro-2-oxonicotinic acid; m.p. 230° C. (dec.) from aqueous acetic acid.

22. 6-(p-Hydroxybenzyl)-1,2-dihydro-2-oxonicotinic acid; a mixture of 15 g. of 6-(p-methoxybenzyl)-1,2-dihydro-2-oxonicotinic acid and 175 ml. of 48% hydrobromic acid is heated at reflux for 24 hours, then cooled. The precipitate is collected, washed with water and dissolved in 200 ml. of 0.5N aqueous sodium hydroxide. The solution is treated with charcoal and filtered. The filtrate is strongly acidified with acetic acid and the resulting precipitate of 6-(p-hydroxybenzyl)-1,2-dihydro-2-oxonicotinic acid is collected by filtration, washed with water and dried; m.p. 276°–278° C. (dec.).

EXAMPLE 24 a. A solution of 1.0 g. of D-(+)-N-(6-benzyl-1,2-dihydro-2-oxonicotinyl)-2-phenylglycine in 10 ml. of tetrahydrofuran is cooled to 0°–5° C. and 0.308 ml. of N-methylmorpholine is added, followed by 0.362 ml. of isobutyl chloroformate. After standing at 0° C. for 12 minutes, the mixture, containing the mixed anhydride of D-(+)-N-(6-benzyl-1,2-dihydro-2-oxonicotinyl)-2-phenylglycine and carbonic acid monoisobutyl ester, is treated with 12 ml. of a 0.452M solution of 6-aminopenicillanic acid trimethylsilyl ester in dioxane [Glombitza, Ann. 673, 166 (1964)]. The mixture is stirred for 1 hour at 0°–5° C., for 2 hours at room temperature, then poured into 50 ml. of water. The aqueous mixture is adjusted to pH 8.2 with saturated aqueous sodium bicarbonate and washed several times with ethyl acetate, the washings being discarded. The aqueous solution is adjusted to pH 2 with 12% hydrochloric acid and extracted with several portions of ethyl acetate. The combined ethyl acetate extracts are washed with 4% hydrochloric acid, several times with water, and are dried and evaporated to provide the free acid product N-(6-benzyl-1,2-dihydro-2-oxonicotinyl)ampicillin. The product is dissolved in 10 ml. of tetrahydrofuran, the solution is filtered and the filtrate is treated with 0.9 ml. of a 50% solution of sodium 2-ethylhexanoate in 1-butanol, then with 25 ml. of ethyl acetate. The resulting precipitate is collected by filtration, washed with ethyl acetate and dried to provide the product N-(6-benzyl-1,2-dihydro-2-oxonicotinyl)ampicillin, sodium salt; $[\alpha]_D^{25}$ +142° (1.025% in methanol). The corresponding free acids, N-(6-benzyl-1,2-dihydro-2-oxonicotinyl)cephalexin and N-(6-benzyl-1,2-dihydro-2-oxonicotinyl)cephaloglycin and the respective sodium salts of these acids, are obtained by the same procedure starting from the trimethylsilyl esters of 6-aminocephalosporanic acid and 7-amino-3-methylceph-3-em-4-carboxylic acid.

b. The phenylglycine starting material for the procedure of paragraph (a) can be prepared by the following method. A mixture of 15.1 g. of D-(−)-2-phenylglycine and 83.5 ml. of hexamethyldisilazane is heated at reflux for 5 hours, filtered to remove any unreacted D-(−)-2-phenylglycine and the filtrate is evaporated at reduced pressure to give D-N-(trimethylsilyl)-2-phenylglycine trimethylsilyl ester which is purified by distillation b.p. 72°–73° C./0.2 mm.

A suspension of 5.9 g. of 6-benzyl-1,2-dihydro-2-oxonicotinic acid in 60 ml. of tetrahydrofuran is treated with 2.04 ml. of thionyl chloride and six drops of dimethylformamide. The mixture is stirred at room temperature for 16 hours, then evaporated at reduced pressure to give a residue of 6-benzyl-1,2-dihydro-2-oxonicotinyl chloride. This acid chloride is dissolved in 90 ml. of tetrahydrofuran, the solution is cooled to 0°–5° C. and trated with an ice-cold solution of 7.59 g. of D-N-(trimethylsilyl)-2-phenylglycine trimethylsilyl ester in 60 ml. of tetrahydrofuran, then with 2.87 ml. of N-methylmorpholine. The mixture is stirred at 0°–5° C. for 1 hour, at room temperature for 2 hours, then poured into 500 ml. of water and the pH adjusted to 8.3 with saturated aqueous sodium bicarbonate. The solution is washed with several portions of ethyl acetate and the washings discarded. The solution is adjusted to pH 2.0 with 12% hydrochloric acid and extracted with several portions of ethyl acetate. The combined acetate extract is washed with water, dried and evaporated at reduced pressure to give D-(+)-N-(6-benzyl-1,2-dihydro-2-oxonicotinyl)-2-phenylglycine; m.p. 142°–145° C. after two crystallizations from acetonitrile; $[\alpha]_D^{25}$ +23.0° (1.025% in tetrahydrofuran).

EXAMPLE 25 a. From the mixed anhydride of D-(+)-N-(6-cyclohexylmethyl-1,2-dihydro-2-oxonicotinyl)-2-phenylglycine and carbonic acid monoisobutyl ester (prepared from 1.0 g. of D-(+)-N-(6-cyclohexylmethyl-1,2-dihydro-2-oxonicotinyl)-2-phenylglycine in 10 ml. of tetrahydrofuran, 0.303 ml. of N-methylmorpholine and 0.356 ml. of isobutyl chloroformate), and 12 ml. of a 0.444M solution of 6-aminopenicillanic acid trimethylsilyl ester, following the procedure of Example 24, there is obtained N-(6-cyclohexylmethyl)-1,2-dihydro-2-oxonicotinyl)ampicillin, sodium salt; $[\alpha]_D^{25}$ +124.3° (1.02% in methanol).

b. The phenylglycine starting material for the procedure of paragraph a) can be prepared by the following method. A solution of 4.0 g. of 6-cyclohexylmethyl-1,2-dihydro-2-oxonicotinic acid in 25 ml. of thionyl chloride is heated at 95°–100° C. for 35 minutes, then diluted with 50 ml. of hexane and cooled. The precipitate of 6-cyclohexylmethyl-1,2-dihydro-2-oxonicotinyl chloride is removed by filtration and washed with hexane. A solution of 2.22 g. of this acid chloride in 40 ml. of tetrahydrofuran is cooled to 0°–5° and treated with an ice-cold solution of 3.11 g. of D-N-(trimethylsilyl)-2-phenylglycine trimethylsilyl ester in 25 ml. of tetrahydrofuran, then with 0.98 ml. of N-methylmorpholine. Using reaction conditions and work-up as in Example 24b, the product is D-(+)-N-(6-cyclohexylmethyl)-1,2-dihydro-2-oxonicotinyl-2-phenylglycine; $[\alpha]_D^{25}$ +21.3°(1.015% in tetrahydrofuran).

EXAMPLE 26

A solution of 1.0 g. of D-(+)-N-(6-cyclohexylmethyl-1,2-dihydro-2-oxonicotinyl)-2-phenylglycine in 10 ml. of tetrahydrofuran is cooled to 0°–5° C. and treated with 0.303 ml. of N-methylmorpholine and 0.356 ml. of isobutyl chloroformate and the mixture is stirred at 0° for 12 minutes. To this solution of the mixed anhydride of D-(+)-N-(6-cyclohexylmethyl-1,2-dihydro-2-oxonicotinyl)-2-phenylglycine and carbonic acid monoisobutyl ester is added an ice cold solution prepared from 733 mg. of 6-aminopenicillanic acid in 10 ml. of dioxane and 1.7 ml. of 2N-aqueous sodium hydroxide in 5 ml. of water. The resulting mixture is stirred for 1 hour at 0° C., for 2 hours at room temperature, then poured into 50 ml. of water. The solution is adjusted to pH 8.2 with saturated aqueous sodium bicarbonate and the solution washed with several portions of ethyl acetate, the washings being discarded. The solution is adjusted to pH 2.0 with 12% hydrochloric acid and extracted with several portions of ethyl acetate. The combined ethyl acetate extract is washed with 4% hydrochloric acid, several times with water, dried and evaporated at reduced pressure to give the free acid product, N-(6-cyclohexylmethyl-1,2-dihydro-2-oxonicotinyl)ampicillin. The product is dissolved in 10 ml. of tetrahydrofuran, the solution is filtered and treated with 1.0 ml. of a 50% solution of sodium 2-ethylhexanoate in 1-butanol, then with 25 ml. of ethyl acetate. The product which separates, N-(6-cyclohexylmethyl-1,2-dihydro-2-oxonicotinyl)ampicillin, sodium salt, is collected by filtration, washed with ethyl acetate and dried; $[\alpha]_D^{25}$ +129.7° (1.03% in methanol).

EXAMPLE 27

Triethylamine (1.26 g.) and trimethylsilyl chloride (1.3 g.) are added to a stirred suspension of 2 g. of cephalexin sodium salt in 75 cc. of tetrahydrofuran cooled in a cold water bath, and the mixture is stirred for 1.5 hours at room temperature. 6-Cyclohexylmethyl-1,2-dihydro-2-oxonicotinyl chloride (1.5 g.) is added and the mixture is stirred over night and poured into water, acidified with hydrochloric acid to pH 2, extracted with ethyl acetate, and the ethyl acetate extracts washed with water, dried over magnesium sulfate and evaporated to dryness. The residual product, N-(6-cyclohexylmethyl-1,2-dihydro-2-oxonicotinyl)cephalexin is dissolved in tetrahydrofuran, and the solution is filtered and treated with 1.9 cc. of sodium 2-ethylhexanoate solution (50% w/v in butyl alcohol). The crystalline product which separates, N-(6-cyclohexylmethyl-1,2-dihydro-2-oxonicotinyl)cephalexin, sodium salt, is collected by filtration and dried.

In a similar manner the folllowing N-(6-substituted-1,2-dihydro-2-oxonicotinyl)cephalexins (and salts) are prepared by reaction of cephalexin sodium salt, trimethylsilyl chloride, and the corresponding 6-substituted-1,2-dihydro-2-oxonicotinyl chloride.

N-[6-(2-Cyclopentenylmethyl)-1,2-dihydro-2-oxonicotinyl]cephalexin.

N-(6-Cyclohexyl-1,2-dihydro-2-oxonicotinyl)cephalexin.

N-[6-(p-Hydroxybenzyl)-1,2-dihydro-2-oxonicotinyl]cephalexin.

N-(6-Benzyl-1,2-dihydro-2-oxonicotinyl)cephalexin.

N-(6-Phenethyl-1,2-dihydro-2-oxonicotinyl)cephalexin.

N-[6-(1-Adamantyl)-1,2-dihydro-2-oxonicotinyl]cephalexin.

N-[6-(o-Methoxybenzyl)-1,2-dihydro-2-oxonicotinyl]cephalexin.

N-[6-(m-Methoxybenzyl)-1,2-dihydro-2-oxonicotinyl]cephalexin.

N-[6-(p-Methoxybenzyl)-1,2-dihydro-2-oxonicotinyl]cephalexin.

N-[6-(p-Chlorobenzyl)-1,2-dihydro-2-oxonicotinyl]cephalexin.

N-(6-Benzyl-1,2-dihydro-1-methyl-2-oxonicotinyl)cephalexin.

N-(2,5,5a,6,7,8,9,9a-Octahydro-2-oxo-1H-indeno[1,2-b]pyridine-3-carbonyl)cephalexin.

N-(cis-2,4b,5,6,7,8,8a,9-Octahydro-2-oxo-1H-indeno[2,1-b]pyridine-3-carbonyl)cephalexin.

N-(6-Furfuryl-1,2-dihydro-2-oxonicotinyl)cephalexin.

N-[6-(2-Thenyl)-1,2-dihydro-2-oxonicotinyl]cephalexin.

N-[6-(2-Pyridyl)-1,2-dihydro-2-oxonicotinyl]cephalexin.

N-[6-(3-Pyridyl)-1,2-dihydro-2-oxonicotinyl]cephalexin.

N-[6-(4-Pyridyl)-1,2-dihydro-2-oxonicotinyl]cephalexin.

N-[6-(2-Furyl)-1,2-dihydro-2-oxonicotinyl]cephalexin.

N-[6-(2-Thienyl)-1,2-dihydro-2-oxonicotinyl]cephalexin.

EXAMPLE 28

Triethylamine (1.26 g.) and trimethylsilyl chloride (1.3 g.) are added to a stirred suspension of 2 g. of cephaloglycin sodium salt in 75 cc. of tetrahydrofuran cooled in a cold water bath, and the mixture is stirred for 1.5 hours at room temperature. 6-Cyclohexylmethyl-1,2-dihydro-2-oxonicotinyl chloride (1.5 g.) is added and the mixture is stirred overnight and poured into water, acidified with hydrochloric acid to pH 2, extracted with ethyl acetate, and the ethyl acetate extracts washed with water, dried over magnesium sulfate and evaporated to dryness. The residual product, N-(6-cyclohexylmethyl)-1,2-dihydro-2-oxonicotinyl)cephaloglycin is dissolved in tetrahydrofuran, and the solution is filtered and treated with 1.9 cc. of sodium 2-ethylhexanoate solution (50% w/v in butyl alcohol). The crystalline product which separates, N-(6-cyclohexylmethyl)-1,2-dihydro-2-oxonicotinyl) cephaloglycin, sodium salt, is collected by filtration and dried.

In a similar manner the following N-(6-substituted-1,2-dihydro-2-oxonicotinyl)cephaloglycins (and salts) are prepared by reaction of cephaloglycin sodium salt, trimethylsilyl chloride and the corresponding 6-substituted-1,2-dihydro-2-oxonicotinyl chloride.

N-[6-(2-Cyclopentenylmethyl)-1,2-dihydro-2-oxonicotinyl]cephaloglycin.

N-(6-Cyclohexyl-1,2-dihydro-2-oxonicotinyl)cephaloglycin.

N-[6-(p-Hydroxybenzyl)-1,2-dihydro-2-oxonicotinyl]cephaloglycin.

N-(6-Benzyl-1,2-dihydro-2-oxonicotinyl)cephaloglycin.

N-(6-Phenethyl-1,2-dihydro-2-oxonicotinyl)cephaloglycin.

N-[6-(1-Adamantyl)-1,2-dihydro-2-oxonicotinyl]cephaloglycin.

N-[6-(o-Methoxybenzyl)-1,2-dihydro-2-oxonicotinyl]cephaloglycin.

N-[6-(m-Methoxybenzyl)-1,2-dihydro-2-oxonicotinyl]cephaloglycin.

N-[6-(p-Methoxybenzyl)-1,2-dihydro-2-oxonicotinyl]cephaloglycin.

N-[6-(p-Chlorobenzyl)-1,2-dihydro-2-oxonicotinyl]cephaloglycin.

N-(6-Benzyl-1,2-dihydro-1-methyl-2-oxonicotinyl)cephaloglycin.

N-(2,5,5a,6,7,8,9,9a-Octahydro-2-oxo-1H-indeno[1,2-b]pyridine-3-carbonyl)cephaloglycin.

N-(cis-2,4b,5,6,7,8,8a,9-Octahydro-2-oxo-1H-indeno[2,1-b]pyridine-3-carbonyl)cephaloglycin. N-(6-Furfuryl-1,2-dihydro-2-oxonicotinyl)cephaloglycin.

N-[6-(2-Thenyl)-1,2-dihydro-2-oxonicotinyl]cephaloglycin.

N-[6-(2-Pyridyl)-1,2-dihydro-2-oxonicotinyl]cephaloglycin.

N-[6-(3-Pyridyl)-1,2-dihydro-2-oxonicotinyl]cephaloglycin.

N-[6-(4-Pyridyl)-1,2-dihydro-2-oxonicotinyl]cephaloglycin.

N-[6-(2-Furyl)-1,2-dihydro-2-oxonicotinyl]cephaloglycin.

N-[6-(2-Thienyl)-1,2-dihydro-2-oxonicotinyl]cephaloglycin.

STARTING MATERIALS

The 6-substituted-1,2-dihydro-2-oxonicotinyl chloride starting materials for the foregoing examples are prepared from the corresponding 6-substituted-1,2-dihydro-2-oxonicotinic acids by heating the acid with thionyl chloride in a manner similar to the oxonicotinyl chloride preparation of Example 4. These are as follows:

6-(2-Cyclopentenylmethyl)-1,2-dihydro-2-oxonicotinyl chloride.

6-Cyclohexyl-1,2-dihydro-2-oxonicotinyl chloride.

6-(p-Hydroxybenzyl)-1,2-dihydro-2-oxonicotinyl chloride.

6-Benzyl-1,2-dihydro-2-oxonicotinyl chloride.

6-Phenethyl-1,2-dihydro-2-oxonicotinyl chloride.

6-(1-Adamantyl)-1,2-dihydro-2-oxonicotinyl chloride.

6-(o-Methoxybenzyl)-1,2-dihydro-2-oxonicotinyl chloride.

6-(m-Methoxybenzyl)-1,2-dihydro-2-oxonicotinyl chloride.

6-(p-Methoxybenzyl)-1,2-dihydro-2-oxonicotinyl chloride.

6-(p-Chlorobenzyl)-1,2-dihydro-2-oxonicotinyl chloride.

6-Benzyl-1,2-dihydro-1-methyl-2-oxonicotinyl chloride.

2,5,5a,6,7,8,9,9a-Octahydro-2-oxo-1H-indeno[1,2-b]pyridine-3-carbonyl chloride.

cis-2,4b,5,6,7,8,8a,9-Octahydro-2-oxo-1H-indeno[2,1-b]pyridine-3-carbonyl chloride.

6-Furfuryl-1,2-dihydro-2-oxonicotinyl chloride.

6-(2-Thenyl)-1,2-dihydro-2-oxonicotinyl chloride.

6-(2-Pyridyl)-1,2-dihydro-2-oxonicotinyl chloride.

6-(3-Pyridyl)-1,2-dihydro-2-oxonicotinyl chloride.

6-(4-Pyridyl)-1,2-dihydro-2-oxonicotinyl chloride.

6-(2-Furyl)-1,2-dihydro-2-oxonicotinyl chloride.

6-(2-Thienyl)-1,2-dihydro-2-oxonicotinyl chloride.

We claim:

1. Amide compounds having the formula

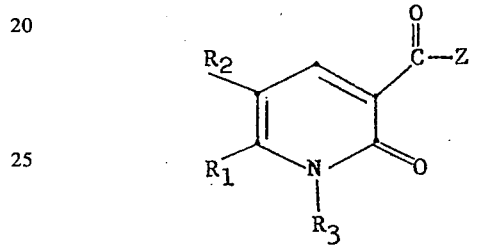

and pharmaceutically-acceptable salts thereof; where $R_1$ is cyclopentylmethyl, cyclopentenylmethyl, cyclohexyl, cyclohexylmethyl, benzyl, phenethyl, adamantyl, methoxybenzyl, hydroxybenzyl, chlorobenzyl, furfuryl, thenyl, pyridyl, furyl or thienyl; $R_2$ is hydrogen or together with $R_1$ represents the group

or the group

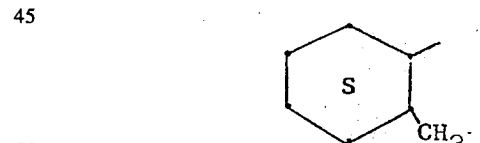

$R_3$ is hydrogen or methyl; and Z is one of two groups having the respective formulas

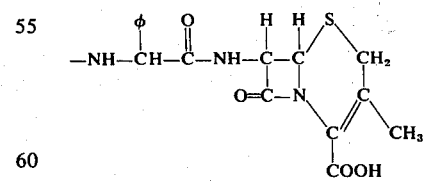

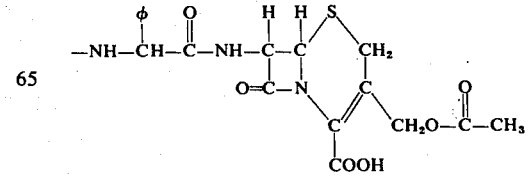

2. A compound according to claim 1 in the form of a free carboxylic acid.

3. A compound according to claim 1 in the form of an alkali metal salt.

4. A compound according to claim 1 which is N-(6-cyclohexylmethyl-1,2-dihydro-2-oxonicotinyl)cephalexin.

5. A compound according to claim 1 which is N-(6-cyclohexylmethyl-1,2-dihydro-2-oxonicotinyl)cephalexin, triethylamine salt.

6. A compound according to claim 1 which is N-(6-cyclohexylmethyl-1,2-dihydro-2-oxonicotinyl)cephaloglycin.

7. A compound according to claim 1 which is N-(6-cyclohexylmethyl-1,2-dihydro-2-oxonicotinyl)cephaloglycin, triethylamine salt.

8. A compound according to claim 1 which is an N-(6-pyridyl-1,2-dihydro-2-oxonicotinyl)cephalexin.

9. A compound according to claim 1 which is an N-(6-pyridyl-1,2-dihydro-2-oxonicotinyl)cephaloglycin.

\* \* \* \* \*

UNITED STATES PATENT AND TRADEMARK OFFICE
CERTIFICATE OF CORRECTION

PATENT NO. : 3,948,903                      Page 1 of 2
DATED     : April 6, 1976
INVENTOR(S) : Leonard Doub and James S. Kaltenbronn It is certified that error appears in the above-identified patent and that said Letters Patent are hereby corrected as shown below:

Column 5, line 11, insert

-- ) -- after "2-ethylhexanoate".

Column 8, line 60, correct the spelling of "trimethyl-".

Column 9, line 6, insert a hyphen after "6" so that it reads:

-- 6-(p-chlorobenzyl)- --.

Column 10, line 4, delete the hyphen between "1" and "H" so that it reads:

-- 1H-indeno --.

"    10, line 20, insert

-- -3- -- between "pyridine" and "carbonyl)".

UNITED STATES PATENT AND TRADEMARK OFFICE
CERTIFICATE OF CORRECTION

PATENT NO. : 3,948,903
DATED : April 6, 1976
INVENTOR(S) : Leonard Doub and James S. Kaltenbronn It is certified that error appears in the above-identified patent and that said Letters Patent are hereby corrected as shown below:

(continued)

Column 12, line 44, correct the spelling of "ethyl".

Column 15, line 4, correct the spelling of "phenyl".

Column 17, line 18, correct the spelling of "pyridine".

Column 18, line 39, correct the spelling of "treated".

Signed and Sealed this

Twentieth Day of July 1976

[SEAL]

Attest:

RUTH C. MASON
Attesting Officer

C. MARSHALL DANN
Commissioner of Patents and Trademarks